(12) United States Patent
Dupelle et al.

(10) Patent No.: US 6,280,463 B1
(45) Date of Patent: Aug. 28, 2001

(54) REDUCING SKIN DAMAGE IN USE OF MEDICAL ELECTRODES

(75) Inventors: Michael R. Dupelle, North Attleboro; Sheldon S. White, Brookline, both of MA (US)

(73) Assignee: ZMD Corporation, Wilmington, DE (US)

( * ) Notice: Subject to any disclaimer, the term of this patent is extended or adjusted under 35 U.S.C. 154(b) by 0 days.

(21) Appl. No.: 09/140,817

(22) Filed: Aug. 26, 1998

(51) Int. Cl.[7] ............................................. A61N 1/00
(52) U.S. Cl. ................................. 607/142; 607/152
(58) Field of Search .......................... 607/142, 149, 607/152, 153; 600/372, 391, 394, 397

(56) References Cited

U.S. PATENT DOCUMENTS

| | | |
|---|---|---|
| 3,702,613 | 11/1972 | Panico et al. . |
| 3,762,420 | 10/1973 | Moore et al. . |
| 3,830,229 | 8/1974 | Johnson ............................ 128/2.6 E |
| 3,845,757 | 11/1974 | Weyer . |
| 3,942,517 | 3/1976 | Bowles et al. ...................... 128/2.1 E |
| 3,989,035 | 11/1976 | Zuehlsdorff . |
| 4,029,086 | 6/1977 | Corasanti . |
| 4,066,078 | 1/1978 | Berg . |
| 4,257,424 | 3/1981 | Cartmell . |
| 4,274,420 | 6/1981 | Hymes . |
| 4,300,575 | 11/1981 | Wilson . |
| 4,367,755 | 1/1983 | Bailey . |
| 4,522,211 | 6/1985 | Bare et al. . |
| 4,526,176 | 7/1985 | Bremer et al. ........................ 128/641 |
| 4,633,879 | 1/1987 | Ong . |
| 4,727,881 | 3/1988 | Craighead et al. . |
| 4,731,926 | 3/1988 | Sibalis ............................ 29/877 |
| 4,771,783 | 9/1988 | Roberts . |
| 4,776,350 | 10/1988 | Grossman et al. . |
| 4,779,630 | 10/1988 | Scharnberg et al. . |
| 4,832,036 | 5/1989 | Cartmell . |
| 4,852,585 | 8/1989 | Heath ................................ 128/798 |

(List continued on next page.)

OTHER PUBLICATIONS

Ralph C. Lee, et al., "Biophysical Mechanisms of Cell Membrane Damage in Electrical Shock", Seminars in Neurology, vol. 15, No. 4; pp. 367–374 (Dec. 1995).

*Primary Examiner*—Jeffrey R. Jastrzab
(74) *Attorney, Agent, or Firm*—Fish & Richardson P.C.

(57) ABSTRACT

A medical electrode assembly includes a conductive electrode, an electrically insulative backing layer on one side of the electrode, an electrically conductive coupling agent in contact with another side of the electrode, an attachment mechanism rigidly connected to a center portion of the electrode, and an electrical conductor connected to the attachment mechanism. The combination of the electrode with the attachment mechanism is constructed with substantial circumferential uniformity such that electrical current provided to the center portion of the electrode through the low-profile attachment mechanism is distributed radially through the electrode in a substantially circumferentially uniform distribution. The electrode is constructed to perform defibrillation or cardioversion. The attachment mechanism is substantially flat and has a low profile. The electrical conductor has a substantially flat, strap-like configuration. A layer of material, which is co-extensive with substantially the entire area of the conductive electrode, causes the insulative backing layer to form a dome while the electrode assembly adheres to a patient's body. In certain embodiments a container surrounds the electrode and the electrically conductive coupling agent. A peel-off layer sealably engages the container through a sealing mechanism. In certain embodiments an electrically conductive sacrificial element is electrically connected with the electrode. The electrically conductive coupling agent contacts the electrode and the sacrificial element, so as to form an anode-cathode cell in which the sacrificial element corrodes and the electrode is protected from corrosion.

30 Claims, 3 Drawing Sheets

U.S. PATENT DOCUMENTS

| | | |
|---|---|---|
| 4,899,754 | 2/1990 | Bly et al. . |
| 4,974,917 | 12/1990 | Kornerup . |
| 4,979,517 | 12/1990 | Grossman et al. . |
| 4,998,536 | 3/1991 | Scharnberg . |
| 5,295,482 * | 3/1994 | Clare et al. .......................... 607/142 |
| 5,330,526 | 7/1994 | Fincke et al. . |
| 5,356,428 | 10/1994 | Way . |
| 5,366,497 | 11/1994 | Ilvento et al. . |
| 5,406,945 | 4/1995 | Riazzi et al. . |
| 5,431,166 | 7/1995 | Macur . |
| 5,456,710 | 10/1995 | Gadsby . |
| 5,462,157 | 10/1995 | Freeman et al. . |
| 5,571,165 | 11/1996 | Ferrari . |
| 5,717,563 | 2/1998 | MacDougall et al. . |
| 5,733,324 | 3/1998 | Ferrari . |
| 5,916,244 * | 6/1999 | Walters ................. 607/142 |
| 6,019,877 | 2/2000 | Dupelle et al. .................. 204/196.11 |

\* cited by examiner

REDUCING SKIN DAMAGE IN USE OF MEDICAL ELECTRODES

BACKGROUND OF THE INVENTION

This invention relates to techniques for improving the effectiveness of medical electrodes and more particularly relates to techniques for improving uniformity of current flow throughout the surface area of medical electrodes and for reducing skin damage in use of such medical electrodes.

Medical electrodes constructed for monitoring of electrical activity within a patient's body typically have a relatively small surface area and are connected to electronic circuitry through an attachment mechanism that may be located at the center of the electrode.

Electrodes constructed for defibrillation or cardioversion typically have a much larger surface area and are connected to a power source through an attachment mechanism that is typically located near an edge of the electrode. Certain defibrillation or cardioversion electrodes, however, are connected to the power source through an attachment mechanism located at the center portion (the center and near-center locations) of the electrode.

For example, an R2 Medical Systems liquid gel, multi-purpose (defibrillation and sensing), disk-shaped electrode is attached to a power source through a wire that is soldered to a rectangular tab that in turn contacts the back of the electrode over a region extending from the periphery of the electrode to the center of the electrode. The point at which the wire is soldered to the rectangular tab is above the center of the electrode. The presence of the rectangular tab detracts from circular uniformity of the electrode/attachment mechanism combination.

Way, U.S. Pat. No. 5,356,428, and Ilvento et al., U.S. Pat. No. 5,366,497 disclose a disk-shaped electrode in the form of a disk-shaped mesh that is soldered to a wire near the center of the mesh. The mesh structure of the electrode detracts from circular uniformity of the electrode/attachment mechanism combination.

Input electrical current typically tends to be concentrated at the peripheries of electrodes, where the resultant reddening or skin damage is usually most noticeable. The Zoll STAT PADZ multi-purpose electrode assembly currently in use, and an electrode described in U.S. Pat. No. 5,330,526 is somewhat effective at providing reduced reddening of skin or skin damage caused by defibrillation, because the total length of the periphery of the electrode is high due to its scalloped or daisy shape.

Ferrari, U.S. Pat. Nos. 5,571,165 and 5,733,324 disclose a defibrillation electrode that is attached to a power source through a multi-strand wire in which the strands are spread out and bonded to a center portion of a rectangular current distributing mat that contacts a center portion of a rectangular electrode. The other side of the electrode contacts one or more silver/silver chloride coatings that are more conductive than the electrode and that have serrated or undulated outer perimeters spaced inwardly from the perimeter of the electrode. The patent states that the silver/silver chloride coatings improve the uniformity of current distribution between the electrode and the skin surface of the patient by reducing current density at the perimeter of the electrode and by increasing the effective perimeter of the electrode. The electrode assembly reduces reddening or skin damage because of the serrated or undulated outer perimeters, and because the central region of the assembly has higher conductivity than more peripheral regions.

Of course, there is a limit to how much of an increase in periphery or how many added layers or thicknesses of such may be practically realized. Increasing the length of the periphery of an electrode by continued surface convolutions eventually leads to convolutions so small or so close to one another that their effect is substantially negated. Increasing the thickness of an electrically conductive layer or adding additional electrically conductive layers could eventually lead to a conductive surface too rigid to accommodate patient contours, which could result in localized differences in the effective distance between the electrode and the patient, thereby resulting in localized power concentrations and reddening.

SUMMARY OF THE INVENTION

One aspect of the invention features a medical electrode assembly that includes a conductive electrode, an electrically insulative backing layer positioned on one side of the electrode, an electrically conductive coupling agent in contact with another side of the electrode, an attachment mechanism rigidly connected to a center portion of the electrode, and an electrical conductor connected to the attachment mechanism. The combination of the conductive electrode with the attachment mechanism is constructed with substantial circumferential uniformity such that electrical current provided to the center portion of the electrode through the attachment mechanism is distributed radially through the electrode in a substantially circumferentially uniform distribution. The conductive electrode is constructed to perform defibrillation or cardioversion, and in certain embodiments the electrode is also constructed to perform pacing and monitoring of electrical activity in a patient. It is believed that the substantial circumferential uniformity of current distribution reduces localized current hot spots.

According to another aspect of the invention, the attachment mechanism is substantially flat and has a low profile. It is believed that this construction can minimize any bulges in the electrode assembly that might interfere with the contact between the electrode assembly and the patient, or that might cause a localized hot spot due to a thinning of the conductive coupling agent at the attachment point that could be caused by such a bulge, or that might result in undesired muscle contractions during defibrillation due to non-uniformity of stiffness of the electrode assembly at the attachment point.

According to another aspect of the invention, the electrical conductor has a substantially flat, strap-like configuration. This construction can further minimize bulges.

Another aspect of the invention features a layer of material, which is not a layer of conductive material constructed for substantial participation in delivery of defibrillation or cardioversion current. The layer of material is co-extensive with substantially the entire area of the conductive electrode. The layer of material does not contain the conductive coupling agent and causes the insulative backing layer to form a dome while the electrode assembly adheres to a patient's body. The layer of material may help to ensure that the electrode plate can be pressed against unusual or convoluted body contours in a manner that provides a good interface between the patient's body and the conductive coupling agent and a good interface between the coupling agent and the electrode plate.

According to another aspect of the invention, a container surrounds the electrode and the electrically conductive coupling agent. A peel-off layer sealably engages the container through a sealing mechanism. This construction provides a low-cost way to keep a coupling agent, especially a low-viscosity coupling agent, from leaking into portions of the electrode assembly such as foam layers. Such low-viscosity coupling agents tend to result in less skin damage than high-viscosity coupling agents.

According to another aspect of the invention, an electrically conductive sacrificial element is electrically connected with the electrode through an attachment mechanism rigidly connected to a center portion of the electrode and to a center portion of the sacrificial element. The electrically conductive coupling agent contacts the electrode and the sacrificial element, so as to form an anode-cathode cell in which the sacrificial element functions as a sacrificial anode that corrodes and the electrode functions as a cathode that is protected from corrosion. The attachment mechanism may be substantially flat and have a low profile, so that the advantages of corrosion protection can be obtained in an electrode assembly in which bulges are minimized that might interfere with the contact between the electrode assembly and the patient.

Numerous other features, objects, and advantages of the invention will become apparent from the following detailed description when read in connection with the accompanying drawings.

DETAILED DESCRIPTION

Figure 1:
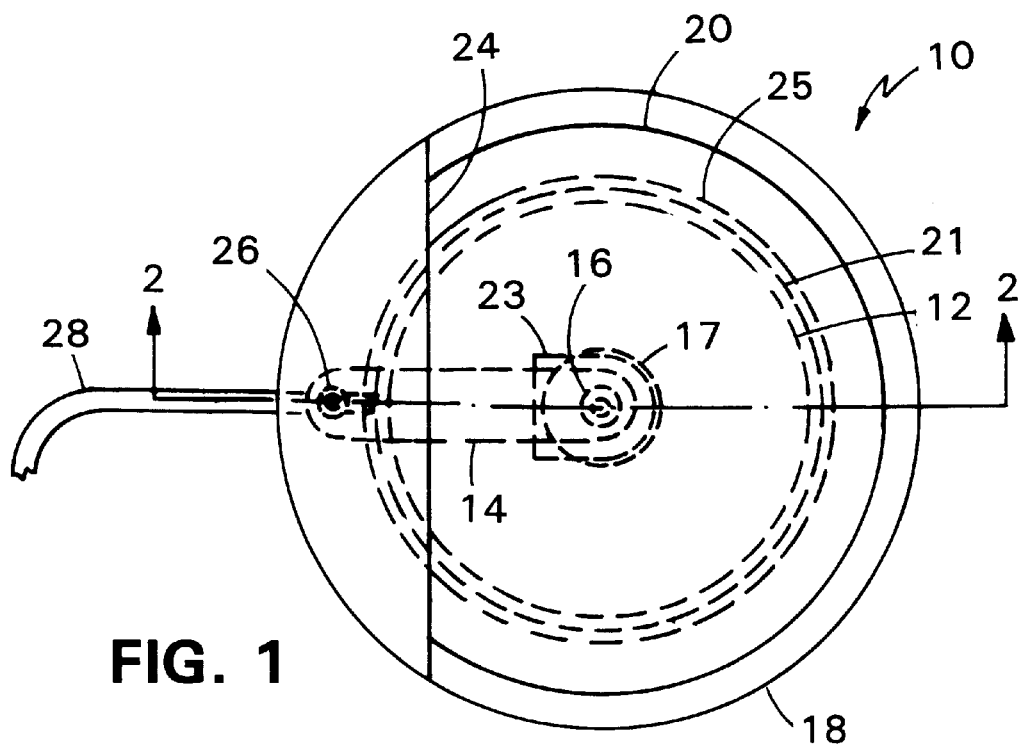
FIG. 1 is a top view of an electrode assembly according to the invention.
Figure 2:
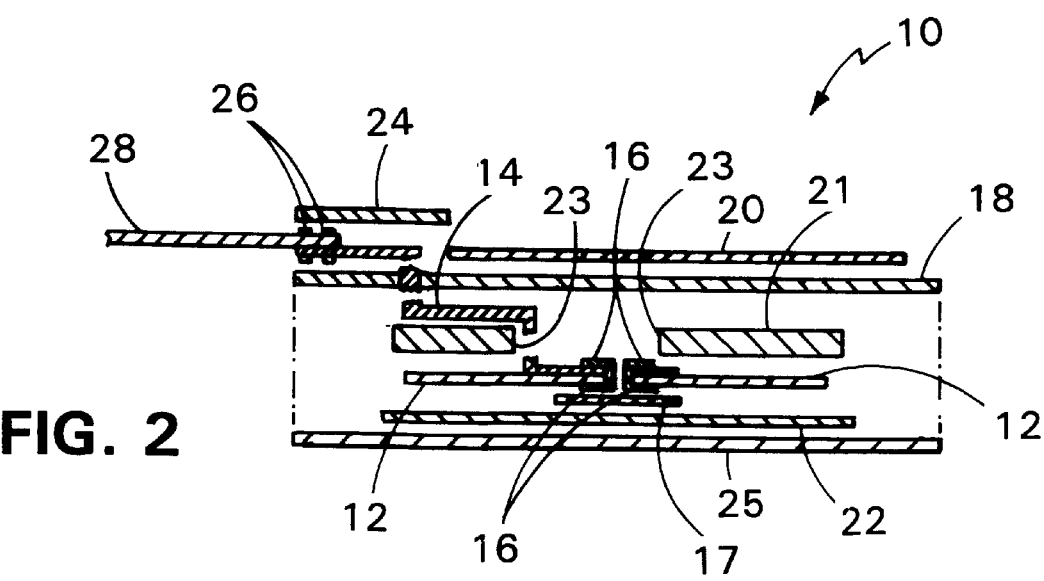
FIG. 2 is an exploded cross-sectional side view of the electrode assembly of FIG. 1 taken along line 2—2.

With reference to FIGS. 1 and 2, multi-purpose electrode assembly 10 can be used for defibrillation, pacing, or monitoring of electrical signals within a patient's body, and avoids damage to a patient's skin resulting from defibrillation. Electrode assembly 10 includes a very thin and non-rigid disk-shaped electrode plate 12 connected to a very thin and non-rigid electrical conductor 14 at the center of electrode plate 12 rather than, for example, the edge of the plate. The thicknesses of electrode plate 12 and electrical conductor 14 are exaggerated in FIG. 2 for clarity. Electrode plate 12 has a surface area sufficiently large for defibrillation or cardioversion, and may be constructed of tin, which is a good material for pacing applications. Alternatively, electrode plate 12 may be constructed of aluminum or silver/silver chloride ink on a substrate or carrier, so as to provide radiolucency. Electrical conductor 14 carries power from a power supply to electrode plate 12 for defibrillation, cardioversion, or pacing, and carries signals from electrode plate 12 to monitoring equipment during procedures involving sensing of electrical signals within the patient's body.

Electrical conductor 14 is attached to electrode plate 12 by a low-profile, substantially circumferentially uniform attachment mechanism 16 such as a grommet, snap, or crimp, which functions as a center feed connection to electrode plate 12. The vertical dimension of attachment mechanism 16 is exaggerated in FIG. 2 for clarity. It is believed that, because of the circumferential uniformity of attachment mechanism 16, and because of the central location of attachment mechanism 16, current distribution within the electrode plate is substantially circumferentially uniform during defibrillation or similar procedures, especially because the electrode has a smooth construction as opposed to, for example, a mesh. It is believed that the circumferential uniformity of current distribution helps to avoid current hot spots. In alternative embodiments, attachment mechanism 16 may itself lack substantial circumferential uniformity, provided, however, that the combination, as a whole, of the conductive electrode together with the attachment mechanism is constructed with substantial circumferential uniformity. As used herein and in the claims, the phrase "substantial circumferential uniformity" encompasses structures having geometric deviations from circumferential uniformity, provided that the structure ensures that the current distribution within the electrode is itself substantially circumferentially uniform.

Electrical conductor 14 is a flat strap or a similar flat conductor, rather than a more bulky wire conductor. It is important that the mechanical connections between flat strap 14 and attachment mechanism 16 and between attachment mechanism 16 and electrode plate 12 be strong so as to avoid loss of energy and localized arcing.

The low profiles of flat strap 14 and attachment mechanism 16 serve to minimize bulges and upsets to the overall profile of conductive electrode plate 12, and thereby help to ensure a good interface and comport between the patient and electrode plate 12 and to ensure against compression and thinning of conductive coupling agent layer 22 at the locations of attachment mechanism 16 and flat strap 14, which might lead to a localized hot spot of electric current. Coupling agent layer 22 may be a high-viscosity gel (commonly mis-described as a "solid gel," although it is not a true solid). It is believed that this minimization of upsets to the profile of electrode plate 12 provides good uniformity of conductivity of coupling agent layer 22 and therefore good uniformity of power distribution over the surface area of electrode plate 12. It is also believed that these low profiles help to reduce localized non-uniformities in stiffness of the electrode assembly at the locations of attachment mechanism 16 and flat strap 14, thereby helping to ensure that these locations provide a good static fit with a patient's body. The minimization of localized non-uniformities in stiffness also helps to ensure that these locations follow movement of the patient's body well during muscle contractions caused by application of electrical current from the conductive electrode to a patient's body for defibrillation or cardioversion, and as a consequence deformation of the electrode assembly is avoided.

Flat strap 14 attaches to wire 28 at attachment point 26, which may be a grommet, snap, or crimp. Attachment point 26, located near the edge of the electrode assembly for ease of manufacture, is sandwiched between insulating backing layer 18 and a section of white foam 24 that covers a portion of the top surface of insulating backing layer 18. White foam section 24 and insulating backing layer 18 may each be about 1/16 inch thick, and insulating backing layer may be about 15 centimeters in diameter. Most of the remainder of the top surface of insulating backing layer is covered by a thin (about 4 mil) MYLAR label 20 (thickness exaggerated in FIG. 2 for clarity). Electrode 12, which consists of metal adhesively attached to a non-conductive backing made of, for example, TYVEK, MYLAR, vinyl, or any other non-conductor that will not react with conductive coupling layer 22, has a thickness of about 7 mil. A thin MYLAR insulator 17 is interposed between attachment mechanism 16 and coupling agent layer 22. A peel-off layer 25 covers coupling agent layer 22. The entire electrode assembly is stored in a sealed package (not shown) prior to use of the electrode assembly, and the electrode assembly may be sterilized within the sealed package.

On the side of electrode plate 12 that is opposite to the patient-facing side, in addition to the usual layer of electrically insulating white foam backing 18, a layer of additional material 21 is provided, such as a sponge made of ⅛-inch thick polyether foam or similar non-conductive material. This layer is co-extensive with, and slightly larger than, the entire area of electrode plate 12, and has a cut-out 23 at its center through which flat strap 14 attaches to electrode plate 12 as shown in FIG. 2.

As electrode assembly 10 is pressed against a patient's body, the patient's body adheres to an adhesive on the bottom surface of the outer portions of insulating backing layer 18 located around the perimeter of layer 21. Layer 21 causes insulating backing layer 18, together with white foam section 24 and MYLAR layer 20, to form a dome. As a consequence of this dome construction, layer 21 applies pressure against the back side of electrode plate 12, which in turn applies pressure to coupling agent layer 22. Thus, layer 21 helps to ensure that electrode plate 12 can be pressed against unusual or convoluted body contours in a manner that provides a good interface between the patient's body and coupling agent layer 22 and a good interface between coupling agent layer 22 and electrode plate 12. It is believed that the presence of layer 21 enhances the initial coupling between coupling agent layer 22 and the patient, and helps to prevent separation of coupling agent layer 22 from the patient's skin that might otherwise result from muscular contractions after application of an electric shock or from unusual body contours such as protruding bone structures. While layer 21 is shown as separate and distinct from insulating backing layer 18, in alternative embodiments layer 21 may be integral with backing layer 18. For example, the central portion of backing layer 18 may be thicker than the peripheral portions so that backing layer 18 forms a dome while the electrode assembly adheres to a patient's body.

The presence of layers 21 and 20 in effect tends to reduce any non-uniformities in distance between electrode plate 12 and the patient as a function of location because of the uniform pressure that layers 21 and 20 cause to be applied across the entire electrode surface. As a consequence, layer 21 serves to reduce concentrations of electric current due to non-uniformity of interfaces between coupling agent layer 22 and the patient's body and between coupling agent layer 22 and electrode plate 12.

In yet another alternative embodiment, backing layer 18 and layer 21 may be combined together as a single layer rather than two separate layers. On the other hand, multiple layers may be advantageous because of incidental or intentional mis-match of grain orientation between the layers (or mis-match between the grain orientation of backing layer 18 and the lack of grain orientation in layer 21 if layer 21 is, for example, a sponge).

Figure 3:
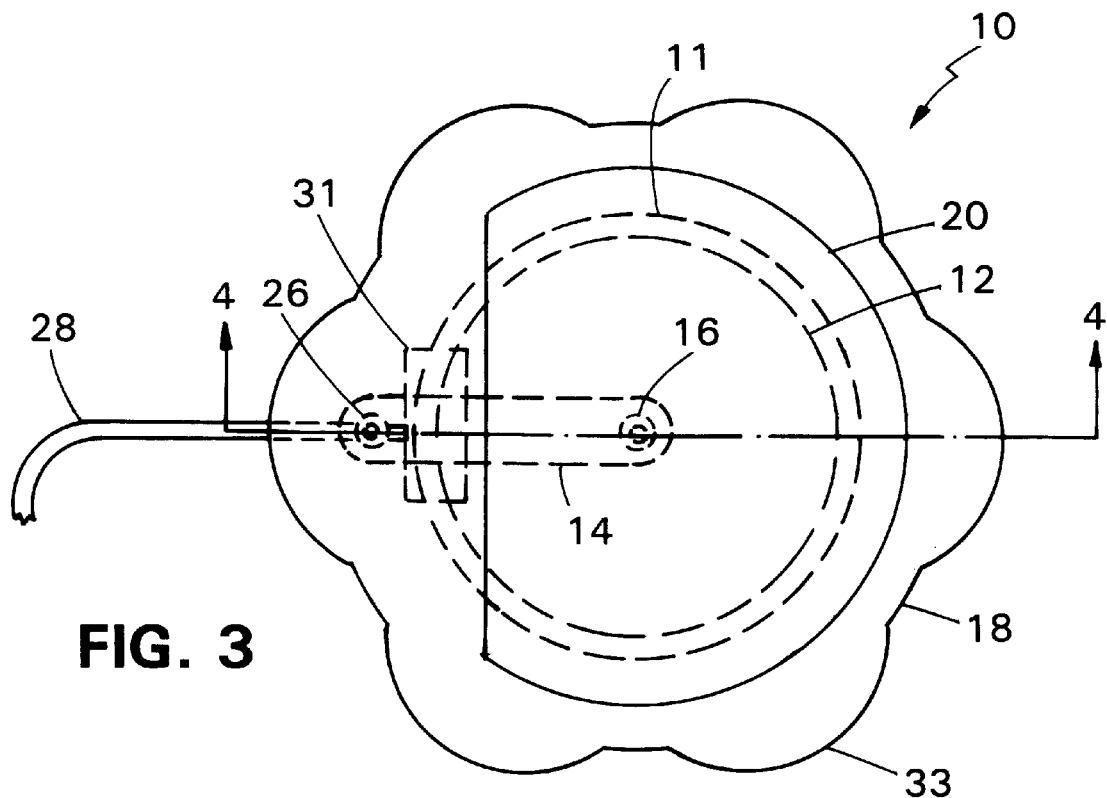
FIG. 3 is a top view of another electrode assembly according to the invention.
Figure 4:
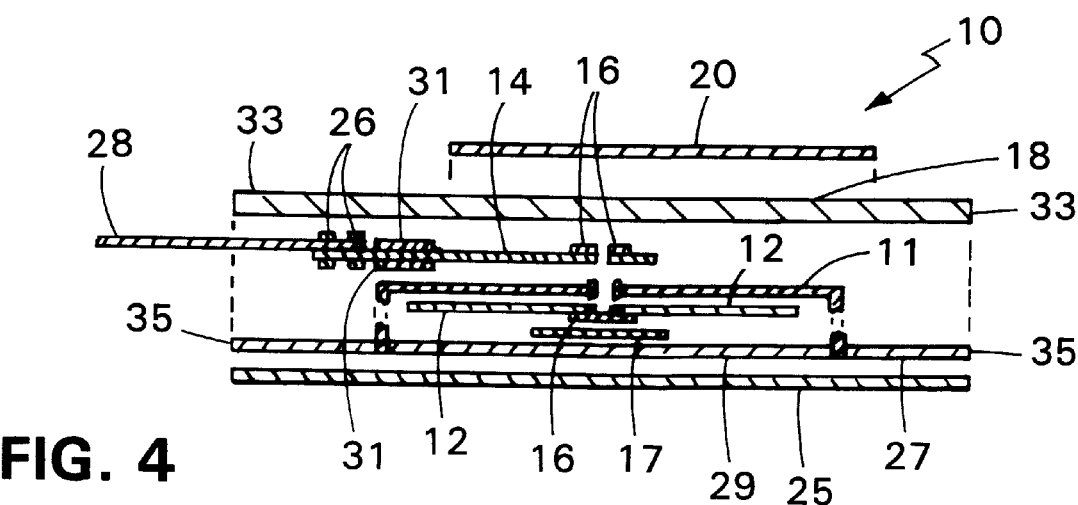
FIG. 4 is an exploded cross-sectional side view of the electrode assembly of FIG. 3 taken along line 4—4.

The principles of the invention are especially useful in connection with electrode assemblies that employ a high-viscosity coupling agent layer because the invention helps to ensure against current concentration problems related to thinning of the high-viscosity coupling agent. For example, the low-profile construction of attachment mechanism 16 and flat strap 14 help to prevent thinning of the high-viscosity coupling agent at the locations of these structures. With reference to FIGS. 3 and 4, in another embodiment of the invention, where like numerals indicate components analogous to those described in connection with FIGS. 1 and 2, a low-viscosity coupling agent (such as a so-called "liquid gel") is employed together with a suitable sponge 29 positioned between electrode plate 12 and the patient's body for containing the low-viscosity coupling agent. Such low-viscosity coupling agents tend to result in less skin damage than high-viscosity coupling agents. A ring 27 of white foam surrounds the perimeter of sponge 29, and wire 28 connects with flat strap 14 at an attachment point 26 located between ring 27 and insulating backing layer 18. A thin MYLAR insulator 17 is interposed between attachment mechanism 16 and sponge 29. Insulating backing layer 18 has tabs 33, and ring 27 has tabs 35. Tabs 35 have an adhesive applied to their bottom surfaces so as to allow the electrode assembly to be adhesively applied to a patient's body. Alternatively, tabs 35 of ring 27 may be eliminated and adhesive may be applied to the patient-facing surfaces of tabs 33 such that tabs 33 create a dome in insulating backing layer 18.

Figure 5:
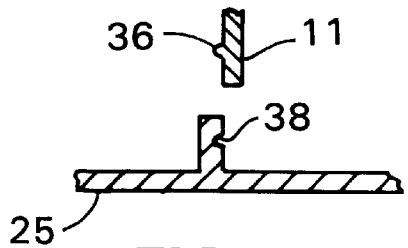
FIG. 5 is a detailed cross-sectional side view of a mating locking mechanism between the plastic container and peel-off layer of the electrode assembly of FIGS. 3 and 4.
Figure 6:
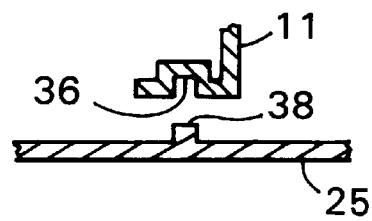
FIG. 6 is a detailed cross-sectional side view of an alternative mating locking mechanism between the plastic container and peel-off layer of the electrode assembly of FIGS. 3 and 4.

The low-viscosity coupling agent is contained by a sealed, non-leaking plastic container 11, which is molded with foam ring 27, that can be easily opened just prior to use of the electrode on a patient by removing peel-off layer 25. Attachment mechanism 16 rigidly affixes container 11 between electrode 12 and the electrical conductor 14. Plastic container 11 helps to keep the low-viscosity coupling agent from leaking into foam ring 27 or backing layer 18. Plastic container 11 and peel-off layer 25 respectively include circular mating locking mechanisms 36 and 38 as shown in FIG. 5 or the alternative embodiment of FIG. 6. This construction provides a low-cost way to keep the coupling agent from leaking into portions of the electrode assembly such as foam layers. Referring again to FIGS. 3 and 4, in order to ensure against the unlikely event of any leakage of the coupling agent from container 11, or as an alternative to provide such a container, double-sided tape pieces 31 may be provided in order to isolate attachment point 26 from the low-viscosity coupling agent.

Figure 7:
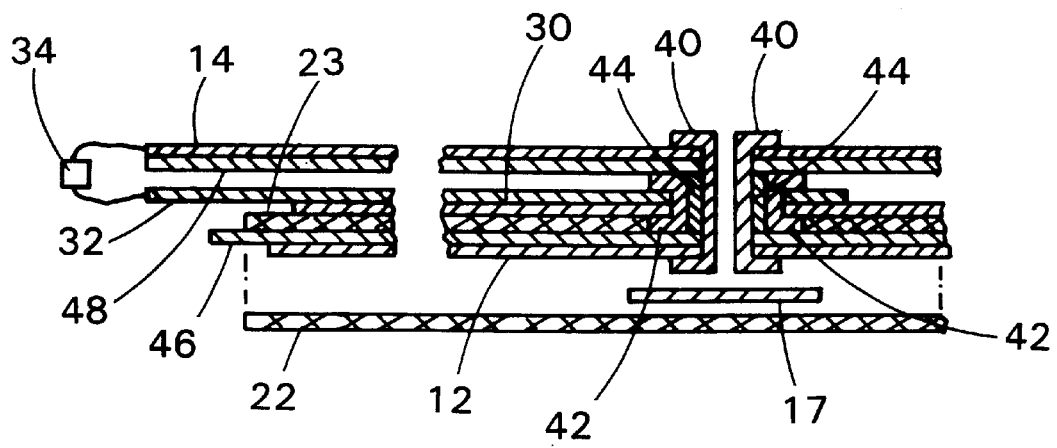
FIG. 7 is an exploded cross-sectional side view of a portion of another electrode assembly according to the invention, incorporating a sacrificial anode.

As shown in FIG. 7, any of the electrode assemblies described above may include a sacrificial anode 30 electrically connected to conductive coupling agent layer 22 in order to protect electrode plate 12 from corrosion, as described in Dupelle et al., U.S. patent application Ser. No. 09/099,256, filed Jun. 18, 1998, the entire disclosure of which is hereby incorporated herein by reference. Sacrificial anode 30 may be a disk located above electrode plate 12 and separated from electrode plate 12 by electrically insulative filter 46 and a coupling agent layer 23. Coupling agent layer 22 contacts coupling agent layer 23 through the periphery of electrically insulative filter 46. A flat, low-profile attachment mechanism to electrode plate 12 and the sacrificial anode 30 consists of, for example, two concentric rivets 40 and 42 (vertical dimension exaggerated), electrically isolated by insulator 44, that provide respective connections of electrode plate 12 and sacrificial anode 30 to respective electrically isolated straps 14 and 32. Straps 14 and 32 are separated by electrical insulator 48, and an impedance device (such as a resistor) or power supply 34 is connected between straps 14 and 32 at a peripheral location on the electrode assembly in order to complete an electrical circuit between electrode plate 12 and sacrificial anode 30 as described in the above-referenced patent application, without substantially increasing the profile of the electrode assembly. Impedance device or power supply 34 is selected in order to prolong an electrochemical reaction between electrode plate 12 and sacrificial anode 30. Strap 14 is also arranged for connection to external circuitry for defibrillation, cardioversion, pacing, and/or monitoring as is described above. In this manner the advantages of corrosion protection can be obtained in an electrode assembly in which bulges are minimized that might interfere with the contact between the electrode assembly and the patient.

The construction shown in FIG. 7 may be employed in an electrode assembly that employs a low-viscosity coupling agent as shown in FIGS. 3 and 4. Rivet 42 of FIG. 7 may, for example, rigidly affix a container 11 of the type shown in FIGS. 3 and 4 between sacrificial anode 30 and strap 32, in order to help to keep the low-viscosity coupling agent from leaking.

There have been described novel and improved apparatus and techniques for improving current distribution uniformity in medical electrodes and reducing skin damage in use of medical electrodes. It is evident that those skilled in the art may now make numerous uses and modifications of and departures from the specific embodiments described herein without departing from the inventive concept. For example, the electrode assemblies described above, which are constructed to avoid localized concentrations of current in the interface between the electrode assembly and the patient, may be used to deliver biphasic waveforms having a substantially rectilinear first phase as described in Lopin et al., U.S. Pat. No. 5,733,310, the entire disclosure of which is hereby incorporated herein by reference, so that the peak current of the waveform can be reduced and as a consequence the likelihood of skin damage can further be reduced. The various features disclosed in the various embodiments described above may be combined, except where the above description indicates otherwise, so as to achieve the advantages of a multiplicity of different techniques of reducing skin damage and improving current distribution uniformity.

What is claimed is:

1. A medical electrode assembly adapted to be applied to the curved surface of a patient, comprising:
    a conductive electrode constructed to perform defibrillation or cardioversion, the electrode being unitary and flexible;
    an electrically insulative flexible backing layer positioned on the side of the electrode away from the surface of the patient;
    an electrically conductive coupling agent in contact with the side of the electrode facing the surface of the patient;
    an attachment mechanism rigidly connected to a center portion of the electrode; and
    a flexible electrical conductor connected to the attachment mechanism,
    wherein the electrode assembly is sufficiently flexible to conform generally to the curved surface of the patient, and
    wherein the combination of the conductive electrode with the attachment mechanism is constructed so that electrical current is delivered by the electrical conductor substantially only to the center portion of the electrode and so that the electrical current provided to the center portion of the electrode is distributed radially through the electrode in a substantially circumferentially uniform distribution.

2. The medical electrode assembly of claim 1 wherein the attachment mechanism itself has a structure that is substantially circumferentially uniform.

3. The medical electrode assembly of claim 1 wherein the conductive electrode is substantially disk-shaped.

4. The medical electrode assembly of claim 1 wherein the conductive electrode is also constructed to perform monitoring of electrical activity in a patient.

5. The medical electrode assembly of claim 1 wherein the conductive electrode is also constructed perform pacing.

6. The medical electrode assembly of claim 5 wherein the conductive electrode is also constructed to perform monitoring of electrical activity in a patient.

7. The medical electrode assembly of claim 1 wherein the conductive electrode comprises a thin, flexible plate.

8. The medical electrode assembly of claim 1 wherein the electrically conductive coupling agent is a high-viscosity coupling agent.

9. The medical electrode assembly of claim 1 wherein the attachment mechanism is substantially flat and has a low profile.

10. The medical electrode assembly of claim 9 wherein the attachment mechanism comprises a grommet.

11. The medical electrode assembly of claim 9 wherein the attachment mechanism comprises a snap.

12. The medical electrode assembly of claim 9 wherein the attachment mechanism comprises a crimp.

13. The medical electrode assembly of claim 1 wherein the electrical conductor connected to the attachment mechanism is substantially flat.

14. The medical electrode assembly of claim 13 wherein electrical conductor has a strap-like configuration.

15. The medical electrode assembly of claim 1, further comprising a layer of material, which is not a layer of conductive material constructed for substantial participation in delivery of defibrillation or cardioversion current, the layer of material being co-extensive with substantially the entire area of the conductive electrode.

16. The medical electrode assembly of claim 15, wherein the layer of material causes the insulative backing layer to form a dome while the electrode assembly adheres to a patient's body.

17. The medical electrode assembly of claim 15 wherein the layer of material is constructed to help provide a good electrical interface between the conductive electrode and the patient's body when the electrode assembly is pressed against convoluted surfaces of the patient's body.

18. A medical electrode of claim 1, wherein the electrical conductor has a substantially flat, strap-like configuration.

19. The medical electrode assembly of claim 18 wherein the strap-like electrical conductor is connected to the center portion of the electrode through a substantially flat, low-profile attachment mechanism rigidly connected to the center portion of the electrode.

20. The medical electrode assembly of claim 18 wherein the attachment mechanism comprises a grommet.

21. The medical electrode assembly of claim 18 wherein the attachment mechanism comprises a snap.

22. The medical electrode assembly of claim 18 wherein the attachment mechanism comprises a crimp.

23. A medical electrode assembly comprising:
    a conductive electrode constructed to perform defibrillation or cardioversion;
    an electrically insulative backing layer positioned on one side of the electrode;

an electrically conductive coupling agent in contact with another side of the electrode;

a substantially flat, low-profile attachment mechanism rigidly connected to a center portion of the electrode;

an electrical conductor connected to the attachment mechanism; and a layer of material, which is not a layer of conductive material constructed for substantial participation in delivery of electrical current to or from a patient's body, the layer of material being co-extensive with substantially the entire area of the conductive electrode;

wherein the substantially flat, low-profile attachment mechanism has a structure that is substantially circumferentially uniform so that electrical current provided to the center portion of the electrode through the low-profile attachment mechanism is distributed radially through the electrode in a substantially circumferentially uniform distribution, and wherein the layer of material causes the insulative backing layer to form a dome while the electrode assembly adheres to a patient's body.

24. A medical electrode assembly comprising:

a conductive electrode constructed to perform defibrillation or cardioversion;

an electrically insulative backing layer positioned on one side of the electrode;

an electrically conductive coupling agent in contact with another side of the electrode;

a substantially flat, low-profile attachment mechanism rigidly connected to a center portion of the electrode;

an electrical conductor connected to the attachment mechanism; and a layer of material, which is not a layer of conductive material constructed for substantial participation in delivery of electrical current to or from a patient's body, the layer of material being co-extensive with substantially the entire area of the conductive electrode;

wherein the substantially flat, low-profile attachment mechanism has a structure that is substantially circumferentially uniform so that electrical current provided to the center portion of the electrode through the low-profile attachment mechanism is distributed radially through the electrode in a substantially circumferentially uniform distribution, and wherein the layer of material is constructed to help provide a good electrical interface between the conductive electrode and the patient's body when the electrode assembly is pressed against convoluted surfaces of the patient's body.

25. A medical electrode assembly comprising:

a conductive electrode constructed to perform defibrillation or cardioversion;

an electrically insulative backing layer positioned on one side of the electrode;

an electrically conductive coupling agent in contact with another side of the electrode; and an electrical conductor connected to the electrode; and a layer of material, which is not a layer of conductive material constructed for substantial participation in delivery of defibrillation or cardioversion current, the layer of material being co-extensive with substantially the entire area of the conductive electrode, wherein the layer of material causes the insulative backing layer to form a dome while the electrode assembly adheres to a patient's body, wherein the electrical conductor is connected to the electrode through an attachment mechanism rigidly connected to the electrode.

26. The medical electrode assembly of claim 25 wherein the layer of material is constructed to help provide a good electrical interface between the conductive electrode and the patient's body when the electrode assembly is pressed against convoluted surfaces of the patient's body.

27. The medical electrode assembly of claim 25 wherein the layer of material is positioned between the conductive electrode and the electrically insulative backing layer.

28. A medical electrode assembly comprising:

a conductive electrode constructed to perform defibrillation or cardioversion;

an electrically insulative backing layer positioned on one side of the electrode;

an electrically conductive coupling agent in contact with another side of the electrode; and an electrical conductor connected to the electrode; and a layer of material, which is not a layer of conductive material constructed for substantial participation in delivery of defibrillation or cardioversion current, the layer of material being co-extensive with substantially the entire area of the conductive electrode, wherein the layer of material causes the insulative backing layer to form a dome while the electrode assembly adheres to a patient's body, wherein the layer of material is substantially sponge-like.

29. The medical electrode assembly of claim 25 wherein the layer of material is distinct from the backing layer.

30. The medical electrode assembly of claim 25 wherein the layer of material is integral with the backing layer.

* * * * *

UNITED STATES PATENT AND TRADEMARK OFFICE
CERTIFICATE OF CORRECTION

PATENT NO. : 6,280,463 B1  
DATED : August 28, 2001  
INVENTOR(S) : Michael R. Dupelle and Sheldon S. White Page 1 of 1

It is certified that error appears in the above-identified patent and that said Letters Patent is hereby corrected as shown below:

<u>Column 8,</u>
Line 10, after "constructed", insert -- to --.
Line 49, "A" should be -- The --.

Signed and Sealed this

Nineteenth Day of March, 2002

Attest:

JAMES E. ROGAN
Director of the United States Patent and Trademark Office

Attesting Officer